US012614264B2

(12) United States Patent
Chandra

(10) Patent No.: US 12,614,264 B2
(45) Date of Patent: Apr. 28, 2026

(54) NON-DESTRUCTIVE METHOD TO PREDICT SHELF LIFE AND MATURITY OF PERISHABLE COMMODITIES

(71) Applicant: Shubham Chandra, Katy, TX (US)

(72) Inventor: Shubham Chandra, Katy, TX (US)

( * ) Notice: Subject to any disclaimer, the term of this patent is extended or adjusted under 35 U.S.C. 154(b) by 525 days.

(21) Appl. No.: 17/744,733

(22) Filed: May 16, 2022

(65) Prior Publication Data

US 2023/0368353 A1     Nov. 16, 2023

(51) Int. Cl.
| | |
|---|---|
| *G06T 7/00* | (2017.01) |
| *B25J 19/02* | (2006.01) |
| *G01N 33/02* | (2006.01) |
| *G06T 7/90* | (2017.01) |

(52) U.S. Cl.
CPC ........... *G06T 7/0002* (2013.01); *B25J 19/021* (2013.01); *G01N 33/025* (2013.01); *G06T 7/90* (2017.01); *G06T 2207/10024* (2013.01); *G06T 2207/20132* (2013.01); *G06T 2207/30188* (2013.01)

(58) Field of Classification Search
CPC ..................... G06T 7/0002; G06T 7/90; G06T 2207/10024; G06T 2207/20132; G06T 2207/30188; B25J 19/021; G01N 33/025; G06V 10/56
See application file for complete search history.

(56) References Cited

U.S. PATENT DOCUMENTS

| | | | |
|---|---|---|---|
| 7,772,139 B2 | 8/2010 | Chandra | |
| 8,367,567 B2 | 2/2013 | Chandra | |
| 8,372,783 B2 | 2/2013 | Chandra | |
| 9,265,187 B2 | 2/2016 | Cavender-Bares | |
| 9,688,464 B2 | 6/2017 | Chandra | |
| 9,710,754 B2 | 7/2017 | Kaye | |
| 11,702,275 B2 | 7/2023 | Chandra | |
| 11,707,768 B2 * | 7/2023 | Zhao ..................... | G06T 7/0004 |
| | | | 209/580 |
| 2021/0000013 A1 * | 1/2021 | Robertson ............. | G06T 7/0004 |

FOREIGN PATENT DOCUMENTS

| | | | | |
|---|---|---|---|---|
| CA | 2896314 C | 6/2020 | | |
| CN | 102707022 A | * 10/2012 | ............. | G06F 30/20 |
| CN | 113204898 A | * 8/2021 | ................ | G01J 3/46 |
| EP | 2938561 B1 | 8/2020 | | |

(Continued)

OTHER PUBLICATIONS

Nambi, Eyarkai & Kulandasamy, Thangavel. (2015). Changes in Machine Dependent RGB Colour Coordinates of Alphonso Mango During Ripening Using Digital Image Processing. trends in bio science. 8. 2072-2076. (Year: 2015).*

(Continued)

*Primary Examiner* — Utpal D Shah
*Assistant Examiner* — Jack Peter Kraynak

(57) ABSTRACT

A non-destructive method to predict the shelf life and maturity of perishable commodities using an intelligent vision system is presented here. The system includes a conventional camera and a vision processor (including shelf-life matrix, defect matrix and maturity matrix specific to each perishable commodity) which automatically determines ready for harvest condition, and the remaining shelf life of the perishable commodity.

1 Claim, 7 Drawing Sheets

1   2   5   6

1 Produce on a tree
2 Imaging Device
3 Maturity Matrix
4 Disease Matrix
5 Analysis Screen
6 Results Screen indicating maturity levels/Remaining Shelf Life

(56) References Cited

FOREIGN PATENT DOCUMENTS

JP          2018096712  A  *  6/2018

OTHER PUBLICATIONS

Manamohana K, Gururaj Bijur, Namesh Malarout, Babita Singla, S. Pavithra, Nithesh Naik. (2020). Applications of Colour Models in the Food Processing Industry: A Systematic Review. PalArch's Journal of Archaeology of Egypt / Egyptology, 17(9), 3496-3512 (Year: 2020).*

Megha.P. Arakeri, Lakshmana, Computer Vision Based Fruit Grading System for Quality Evaluation of Tomato in Agriculture industry, Procedia Computer Science, vol. 79, 2016, pp. 426-433, ISSN 1877-0509 (Year: 2016).*

Nambi, Eyarkai. (2015). Studies on Colour Behaviour of Alphonso Mangoes during Ripening Using CIE-Lab Colour Space. Trends in bio science. 8. 2068-2071. (Year: 2015).*

Thor, Nandan, (2017), Using Computer Vision to Build a Predictive Model of Fruit Shelf-Life. Thesis. https://doi.org/10.15368/theses. 2017.30 (Year: 2017).*

* cited by examiner

1 Produce at a distribution/retail center
2 Imaging Device
3 Shelf Life Matrix
4 Defect Matrix
5 Maturity Matrix
6 Analysis Screen
7 Results Screen indicating maturity levels/Remaining Shelf Life 1 Produce on a tree
2 Imaging Device
3 Maturity Matrix
4 Disease Matrix
5 Analysis Screen
6 Results Screen indicating maturity levels/Remaining Shelf Life

NON-DESTRUCTIVE METHOD TO PREDICT SHELF LIFE AND MATURITY OF PERISHABLE COMMODITIES

TECHNICAL FIELD

The present disclosure relates to a method and computer-based apparatuses to predict the shelf life and maturity of commodities such as perishables, including fruits, vegetables, seeds, meat, fish, freezer dried products, beverages and pharmaceutical drugs. In lieu of this patent application and research, no federally/Government sponsored research or development-based funding was used.

BACKGROUND OF THE INVENTION

Today we harvest about four billion metric tons of crop per year, yet 33-57% of this is food is thrown away every year. In low-income countries, farmers lose about 40% of all the food they grow. For high-income countries, 20 pounds of food/person is wasted each month. While most of these food losses are happening at the farmgate, distribution and retail stores, the food waste is primarily happening at the consumption stage. The shelf life, defined as the length of time that a commodity may be stored without becoming unfit for use, consumption, or sale, becomes of paramount importance. Maturity is considered as one of the most important quality determination factors in harvesting at the right time and for the postharvest handling of produce. The capability to know the shelf life will lead to better decision making. Batches which have a longer shelf life, could be used for exports and longer transit markets, while those with shorter shelf life could be directed to more localized markets. This understanding of the shelf life of the produce will help in preventing these losses and wastages, reducing costs, and improving overall freshness. Perishable commodities, such as fruits, vegetables, seeds, freeze dried products, meats, fish, and pharmaceutical products each have a unique shelf life. The shelf-life prediction methods collect data and subsequently use algorithms to estimate the time to reach end of shelf life. Some of this data is based upon the following parameters:

1. Brix value
2. Ethylene generated
3. Taste
4. Bruising intensity
5. Firmness
6. Color
7. Visual defects
8. Initial growing conditions
9. Temperature
10. Humidity
11. Smell
12. Chemical secretions The methods for shelf-life prediction can be categorized into two main categories:

a. Destructive Methods (Chemical Analysis/Static Testing)
b. Non-Destructive Methods (Temperature/Humidity Monitoring, Imaging including hyperspectral, Spectroscopy, and Acoustic Resonance Imaging.

There are several challenges associated with shelf-life prediction methods, one of the major challenges being each piece of produce is unique. A pear from one orchard on one specific tree on one specific branch may look, feel, and taste completely different than a neighboring pear. As this pear naturally changes—it oxidizes, changes color, changes texture, changes quality etc. There is also the added complexity of the surface geometry, and texture which makes it even harder to predict shelf life. Some of the other challenges include the variability with regards to harvesting of the fruit, wherein local inherent knowledge, passed down the generations, which have sometimes never been documented, lead to time for harvest, making it inconsistent with regards to 'perfect' harvest times. Inconsistent cold chain, lack of postharvest procedures, inconsistent ethylene ripening techniques, and inconsistent quality procedures, are all the challenges associated with predicting the shelf life of the fruit/vegetables. At this time there is no accurate way to predict the actual remaining shelf of a produce commodity. While the use of tool, "the rule of ten", Q10, which is the factor by which rate of spoilage increases when the temperature is raised by 10C has been well documented. However, this does not take into account the physical imperfections, variation in maturity and color, and bruising and injuries to the produce, which have a big impact on the overall shelf life of the produce.

With these variabilities in the supply chain into perspective, it is very difficult to commercially specify the shelf life and freshness of fruits and vegetables. This method optimizes the management of the fruits and vegetables/meat supply chain, by empowering the farmers, distribution centers, retails stores, and the home consumers by providing with critical remaining shelf-life information, to make informed decisions, which ensures reduction in supply chain risks, reduction in food waste and losses, and overall reduction in carbon footprint. Components of this methodology can be either embedded in robotics systems/autonomous drones at the farmgate, allowing for easier prediction of harvest dates, and reduction in losses on the tree/plant of fruits and vegetables, and eventual retrieval of the same. Such methods will be useful in accurately predicting the shelf life of food items, when embarking on long duration missions such as space travel. Certain components of this methodology can also be used for finding anomaly detection

SUMMARY OF THE INVENTION

In accordance with the purpose(s) of the invention, as embodied and broadly described herein, this disclosure, in one aspect, relates to Non-Destructive method of predicting the shelf life of perishables using a combination of image analysis, temperature and humidity data, bruising intensity, and overall browning index. The image analysis is done using the CIELAB color space. The CIELAB color space, also referred to as L*a*b*, is a color space defined by the International Commission on Illumination in 1976. It expresses color as three values: L* for perceptual lightness, and a* and b* for the four unique colors of human vision: red, green, blue, and yellow. CIELAB was intended as a perceptually uniform space, where a given numerical change corresponds to a similar perceived change in color.

The important thing for the CIELAB color space is that it is device-independent, "standard observer" model. The colors it defines are not relative to any particular device such as a computer monitor or a printer, but instead relate to the CIE standard observer which is an averaging of the results of color matching experiments under laboratory conditions.

The CIELAB space is three-dimensional, and covers the entire range of human color perception, or gamut. It is based on the opponent color model of human vision, where red and green form an opponent pair, and blue and yellow form an opponent pair. The lightness value, L*, also referred to as "Lstar," defines black at 0 and white at 100. The a* axis is relative to the green-red opponent colors, with negative values toward green and positive values toward red. The b* axis represents the blue-yellow opponents, with negative numbers toward blue and positive toward yellow.

The a* and b* axes are unbounded and depending on the reference white they can easily exceed ±150 to cover the human gamut. Nevertheless, software implementations often clamp these values for practical reasons. For instance, if integer math is being used it is common to clamp a* and b* in the range of −128 to 127.

The hue of a color is quantified by its hue angle $h_{ab}$ in the a*b*-plane, given in degrees (°). The hue angle of a color can be calculated from the color coordinates:

$$h_{ab} = \arctan\left(\frac{b^*}{a^*}\right).$$
Equation 1

Chroma is the amount of saturation of a color. Colors of high chroma are said to be clear, bright or brilliant. Dull (pastel) colors have a low chroma.

$$C_{ab} = \sqrt{a^{*2} + b^{*2}}$$
Equation 2.

BRIEF DESCRIPTION OF THE DRAWINGS

Reference is made to the accompanying drawings in which is shown an illustrative embodiment of the invention, from which its novel features and advantages will be apparent.

DESCRIPTION OF THE PREFERRED EMBODIMENTS

Figure 1:
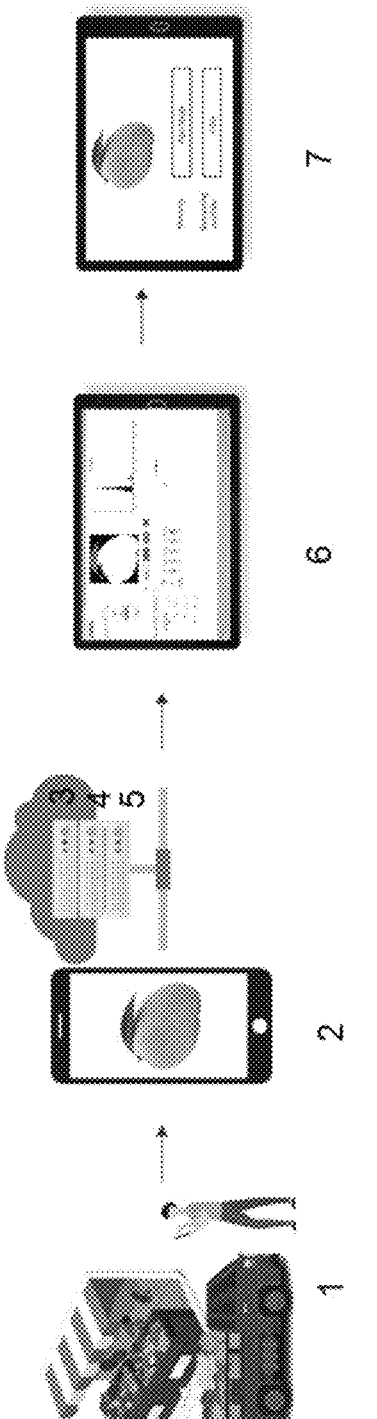
FIG. 1 is a simplified illustration of the Non-Destructive Method to predict the maturity and the Remaining Shelf-Life Prediction methodology.

Referring to FIG. 1, it will be seen that an illustrative includes there is produce at a distribution/retail center 1, an image of the produce is captured via an imaging device 2, three matrices, 3 Shelf Life Matrix, 4 Defect Matrix, and 5 is the Maturity Matrix either resides on the cloud server or on the imaging device itself, 6 is the analysis based upon the comparison of the image with the three matrices, 3, 4 & 5. 7 is the results panel which documents the maturity stage and remaining shelf life of the produce.

Figure 2:
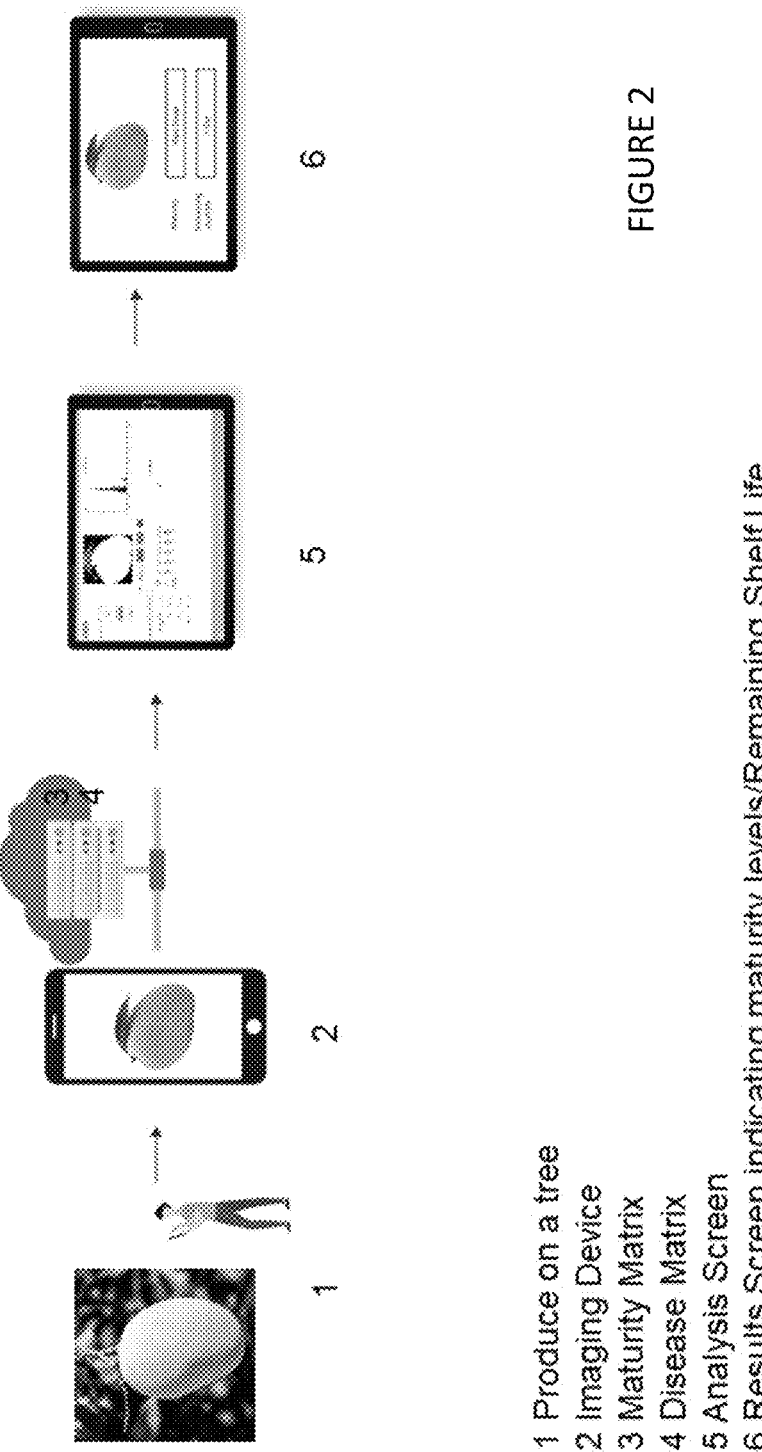
FIG. 2 is a simplified illustration of the Non-Destructive Method to predict the ready for harvest and documenting disease information of the fruit while on the tree. maturity and the Remaining Shelf-Life Prediction methodology.

Referring to FIG. 2, it will be seen that an illustrative includes there is produce on a tree 1, an image of the produce is captured via an imaging device 2, 3 is the Maturity Matrix, 4 is disease matrix which either reside on the cloud server or on the imaging device itself, 5 is the analysis based upon the comparison of the image with the three matrices, 6 is the results panel which documents the maturity stage and determines if the produce is ready for harvest or not. Based upon the disease matrix, if the produce is found to be diseased, the results panels will state the produce is diseased.

Figure 3:
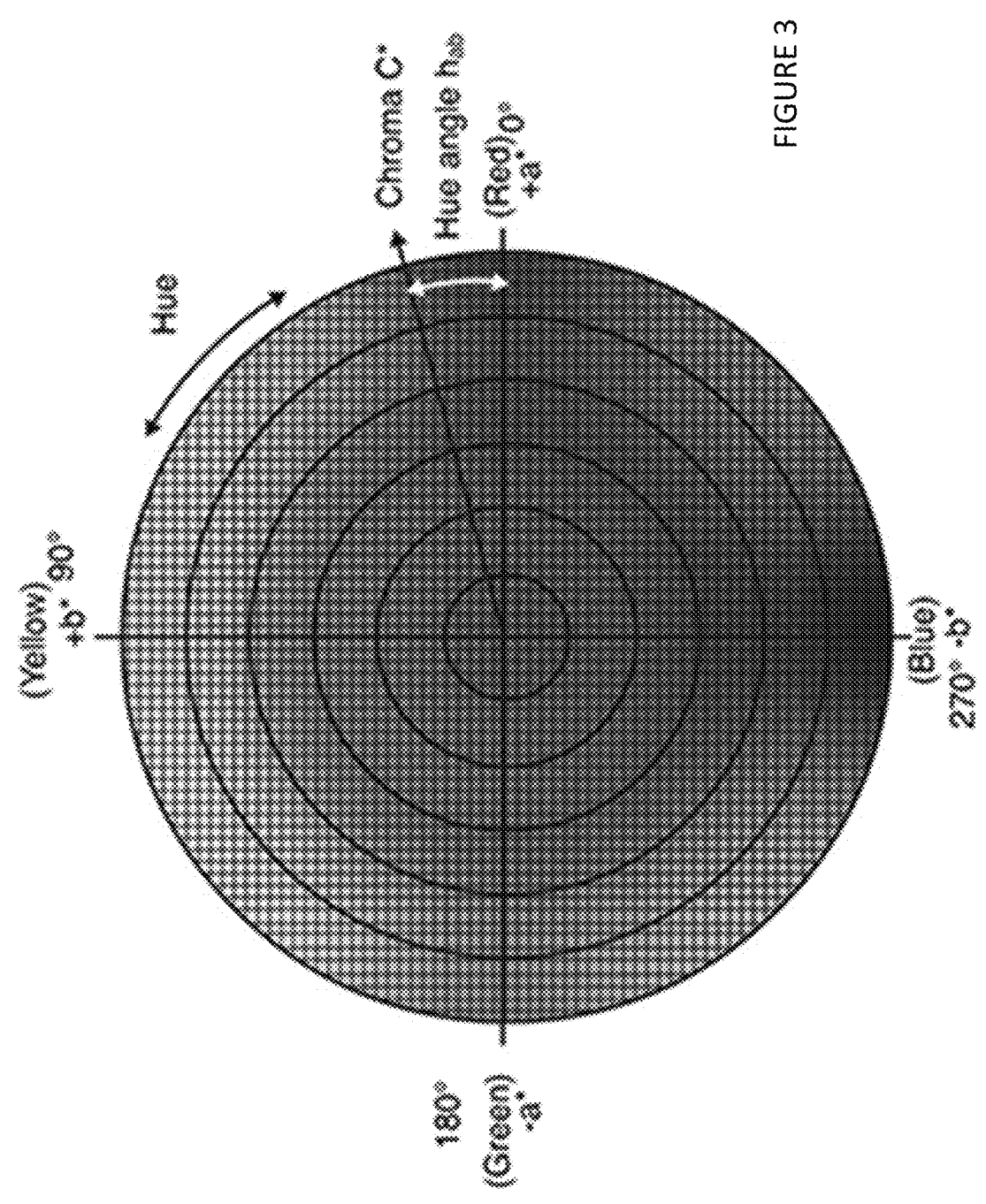
FIG. 3 is a simple illustration of the CIELAB parameters.

Referring to FIG. 3, the CIELAB color chart is explained, with the depiction of Hue 1, and Chroma 2.

Figure 4A:
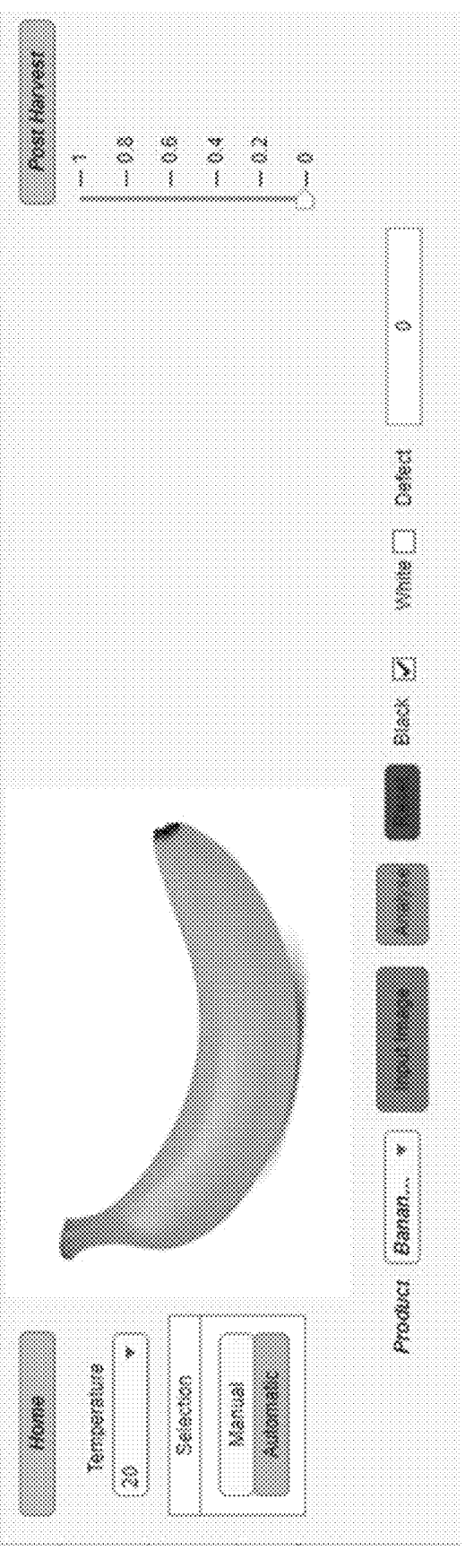
FIG. 4a is an illustration of the process to analyze the state of the produce (in this case banana).

Referring to FIG. 4a, the analysis for ready for harvest for fruits and vegetables is demonstrated.

Figure 4B:
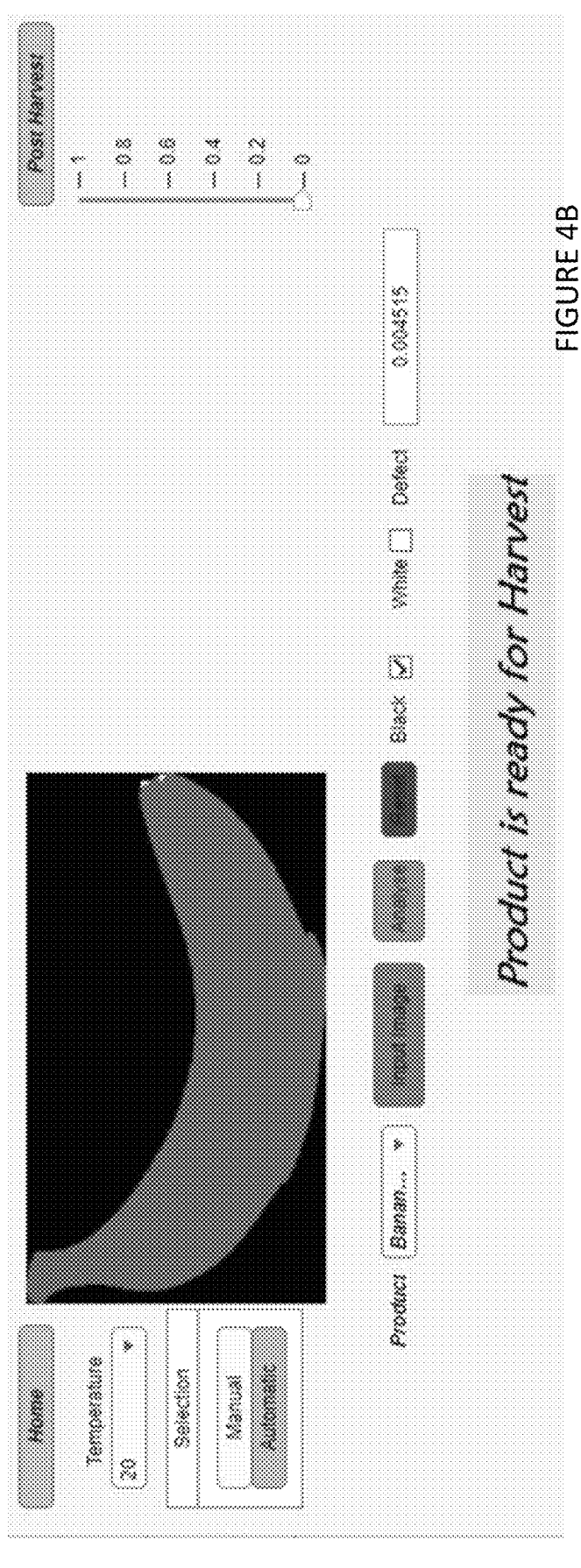
FIG. 4b is the analysis result of the scanned banana predicting that the banana is ready for harvest.

Referring to FIG. 4b, the results for the produce item are demonstrated.

Figure 5A:
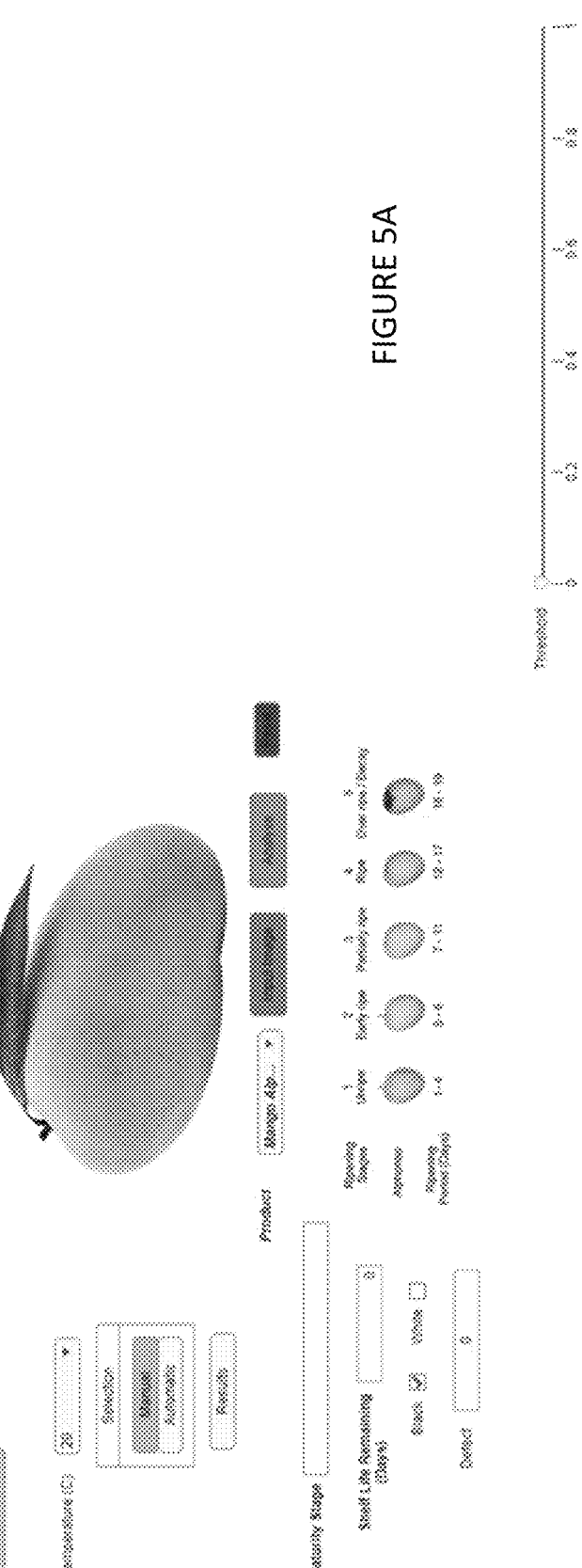
FIG. 5a is an illustration of the process to analyze the Remaining Shelf Life of the produce (in this case mango).

Referring to FIG. 5a, the analysis for remaining shelf life for fruits and vegetables is demonstrated.

Figure 5B:
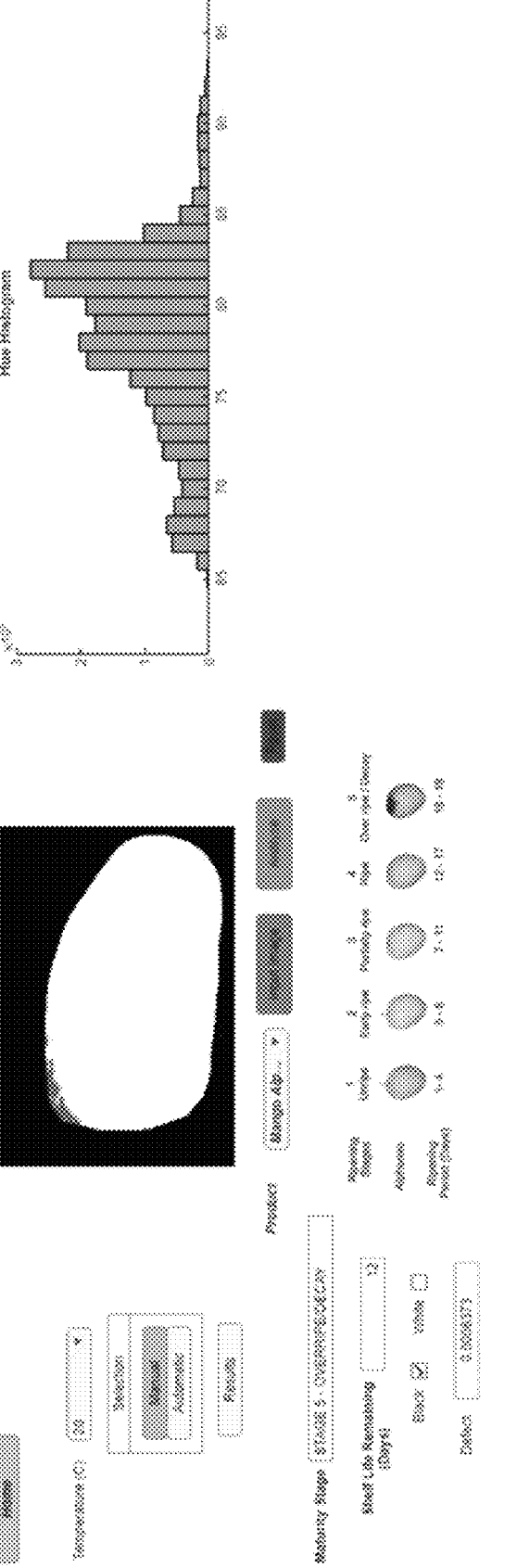
FIG. 5b is the analysis result of the scanned mango predicting the maturity stage and the shelf life remaining.
Figure 5B:
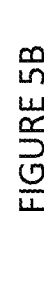

Referring to FIG. 5b, the results for the remaining shelf life and maturity of the produce item are demonstrated.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, example methods and materials are now described.

As used in the specification and the appended claims, the singular forms "a," "an" and "the" include plural referents unless the context clearly dictates otherwise.

In one aspect, the present disclosure provides a method for predicting the ready for harvest condition of fruits and vegetables, the method comprising generating an image of the said fruits/vegetables, resizing and cropping the image, separating the red, green and blue channels from the image, and converting the image to CIELAB color space and identifying parameters such as, 1*, a* and b*, hue, and chroma, and comparing with the produce specific Maturity Matrix to predict harvest ready or not, FIGS. 4a and 4b. In another aspect, the present disclosure provides a method for predicting the remaining shelf life of the fruits and vegetables, the method comprising generating an image of the said fruits/vegetables, resizing and cropping the image, separating the red, green and blue channels from the image, and converting the image to CIELAB color space and identifying parameters such as, 1*, a* and b*, hue, and chroma, and comparing with the produce specific Maturity Matrix, Shelf Life Matrix and the Defect Matrix to predict remaining shelf life of the fruit/vegetable, FIGS. 5a and 5b.

In another aspect, the present disclosure provides a method for predicting the remaining shelf life of the fruits and vegetables, the method comprising generating an image of the said fruits/vegetables, resizing and cropping the image, separating the red, green and blue channels from the image, and converting the image to CIELAB color space and identifying parameters such as, L*, A* and B*, hue, and chroma, and comparing with the produce specific Maturity Matrix, Shelf Life Matrix and the Defect Matrix to predict remaining shelf life of the fruit/vegetable, FIGS. 5a and 5b.

EXAMPLES

The invention will now be illustrated, but not limited, by reference to the specific embodiments described in the following examples.

Example 1

A mango photo is taken as in FIG. 5a.

Resize Image to fixed size of 1816×2688. Next crop image to obtain minimum area image. To crop the image, we first check if the image is 3D, if yes, then convert to 2D gray image. Convert 2D gray image to binary black and White Image. Calculate areas and bounding boxes of the objects inside the black and white image. Find the maximum area object from calculated areas and corresponding bounding box for that object. Crop the image using the found bounding box.

One draws a free selection region of interest on the image or automatically select the fruit/vegetable. All values of pixels in original image except masked pixels are set to zero. Drawn region of interest is deleted. The overall image analysis is conducted thereafter. Based upon the selected area of interest, separate red, green, blue channels from the original image are captured. The masked image is converted to CIELAB color space. The L, A and B values are separated. Remove all lab and color values which are zero. Calculate HUEMIN, HUEMAX and hue. Histogram of Hue is plotted. There are 7 scenarios, and the image is analyzed based upon that:

Based on L max
Based on L min
Based on A max
Based on A min
Based on B max
Based on B min
Based on Average values The based value is found and then corresponding to that value rest of the value is found. Data is shown in Table 1 below.

TABLE 1

| | | | | | | | | | | |
|---|---|---|---|---|---|---|---|---|---|---|
| CIELAB and RGB Parameters for the Mango Photo taken | | | | | | | | | | |
| R | G | B | L | A | B | HUE | HUEMIN | HUEMAX | Defect % | |
| 255 | 255 | 254 | 89.4302 | −2.4083 | 60.2537 | 92.2888 | 92.2888 | 92.2888 | 0 | |
| 240 | 180 | 74 | 52.7246 | 23.6763 | 60.1477 | 68.5136 | 68.5136 | 68.5136 | 0 | |
| 255 | 255 | 255 | 65.9943 | 34.4015 | 71.5891 | 64.3338 | 64.3338 | 64.3338 | 0 | |
| 255 | 255 | 255 | 87.4243 | +3.6636 | 63.9843 | 93.277 | 93.277 | 93.277 | 0 | |
| 255 | 255 | 255 | 82.8101 | 7.3091 | 78.1241 | 84.6551 | 84.6551 | 84.6551 | 0 | |
| 255 | 255 | 255 | 88.8711 | −1.5904 | 58.2346 | 91.5643 | 91.5643 | 91.5643 | 0 | |
| 239 | 198 | 119 | 69.7938 | 14.9872 | 71.1195 | 78.1 | 78.1 | 78.1 | 0 | |

Calculate Maturity by Reading the maturity file data, which is shown in Table 2. First the HUEMAX from Table 1 is matched with HUEMAX from Table 2. For matching we calculate difference of calculated HUEMAX with each stage's HUEMAX from Table 2 and then taking the stage with least difference. After that we match HUEAVG using same above technique. Then we check if day calculated from HUEMAX and HUEAVG are same. If same, then that's the maturity stage if not same then we will compare AMIN and AMAX further to decide maturity stage.

Suppose the HUEMAX and HUEAVG matched with Stage 3- to Stage 5 respectively, so now we will match AMIN and AMAX from stage 3 to stage 5

Match calculated AMAX with Table 2's AMAX for stage 3. Match calculated AMIN with Table 2's AMIN for stage 3. Find and save value which has least difference from above two values Repeat above three steps for all the stages from stage 3 to stage 5. This gives total 3 least values corresponding to stages 3, 4 and 5.

Find the minimum difference value among all the calculated values among above three values.

This is our maturity stage that is closest to our calculated value. We find the maturity stage of the Mango is Stage 5.

TABLE 2

| | | | | | |
|---|---|---|---|---|---|
| Maturity Matrix - Maturity Data for Mango (ready to harvest) | | | | | |
| Stage | AMAX | AMIN | HUEMAX | HUEMIN | HUEAVG |
| STAGE 1- UNRIPE | −2.8898 | −23.4647 | 116.3376 | 95.3556 | 114.673 |
| STAGE 2- EARLY RIPE | 3.1741 | −17.9865 | 111.0686 | 86.355 | 100.4461 |
| STAGE 3 - PARTIALLY RIPE | 14.4234 | −8.1765 | 96.4347 | 78.7858 | 90.5588 |
| STAGE 4 - RIPE | 19.6962 | −2.4537 | 91.8921 | 74.6495 | 85.2115 |
| STAGE 5 - OVERRIPE/ DECAY | 20.8387 | −1.7419 | 99.0804 | 27.0151 | 81.096 |

Read the shelf life data, which is shown in Table 3. First the HUEMAX from Table 1 is matched with HUEMAX from Table 3. For matching we calculate difference of calculated HUEMAX with each stage's HUEMAX from Table 3 and then taking the stage with least difference.

After that we match HUEAVG using same above technique. Then we check if day calculated from HUEMAX and HUEAVG are same. If same then that's the maturity stage if not same then we will compare AMIN and AMAX further to decide maturity stage.

Suppose the HUEMAX and HUEAVG matched with Days 7 to 9 so now we will match AMIN and AMAX for these days.

Match calculated AMAX with Table 3's AMAX for Day 7. Match calculated AMIN with Table 2's AMIN for day 7. Find and save value which has least difference from above two values Repeat above three steps for all the days from Day 7 to Day 9. This gives total 3 least values corresponding to days 7, 8 and 9. Find the minimum difference value among all the calculated values among above three values. This is our shelf life that is closest to our calculated value. We find the remaining shelf life of the Mango by subtracting from the total number of shelf life to the matches shelf life. The remaining shelf life is found to be 12 days.

TABLE 3

| | | | | | |
|---|---|---|---|---|---|
| Shelf-Life Matrix - Shelf Life Data for Mango (Day 1 to Day 19) | | | | | |
| DAYS | AMAX | AMIN | HUEMAX | HUEMIN | HUEAVG |
| 1 | −9.34464 | −22.9436 | 120.3509 | 106.1455 | 114.7813 |
| 2 | −9.54247 | −26.1497 | 109.3918 | 98.49451 | 104.5212 |
| 3 | 7.30502 | −11.28 | 99.13905 | 82.8271 | 93.42326 |
| 4 | 3.773863 | −11.6731 | 100.551 | 87.0441 | 93.45909 |

TABLE 3-continued

| Shelf-Life Matrix - Shelf Life Data for Mango (Day 1 to Day 19) | | | | | |
|---|---|---|---|---|---|
| DAYS | AMAX | AMIN | HUEMAX | HUEMIN | HUEAVG |
| 5 | 3.343492 | −19.2558 | 109.0611 | 86.53275 | 101.2904 |
| 6 | 3.343492 | −19.2558 | 109.0611 | 86.53275 | 90.63397 |
| 7 | 14.42341 | −8.17647 | 96.43475 | 78.78582 | 90.63397 |
| 8 | 14.42341 | −8.17647 | 96.43475 | 78.78582 | 90.63397 |
| 9 | 14.42341 | −8.17647 | 96.43475 | 78.78582 | 90.63397 |
| 10 | 14.42341 | −8.17647 | 96.43475 | 78.78582 | 90.63397 |
| 11 | 14.42341 | −8.17647 | 96.43475 | 78.78582 | 90.63397 |

TABLE 3-continued

| Shelf-Life Matrix - Shelf Life Data for Mango (Day 1 to Day 19) | | | | | |
|---|---|---|---|---|---|
| DAYS | AMAX | AMIN | HUEMAX | HUEMIN | HUEAVG |
| 12 | 19.96494 | −3.41899 | 100.3274 | 71.90615 | 84.92258 |
| 13 | 19.96494 | −3.41899 | 100.3274 | 71.90615 | 84.92258 |
| 14 | 19.96494 | −3.41899 | 100.3274 | 71.90615 | 84.92258 |
| 15 | 19.96494 | −3.41899 | 100.3274 | 71.90615 | 84.92258 |
| 16 | 19.96494 | −3.41899 | 100.3274 | 71.90615 | 84.92258 |
| 17 | 19.96494 | −3.41899 | 100.3274 | 71.90615 | 84.92258 |
| 18 | 21.48506 | −1.74188 | 99.08042 | 27.01506 | 80.93653 |
| 19 | 21.48506 | −1.74188 | 99.08042 | 27.01506 | 80.93653 |

TABLE 4

| Defect Matrix - Data for Browning Index for Mango | | | |
|---|---|---|---|
| Categories | LowerRange | UpperRange | Shelf Life Loss (%) |
| No Browning | 0 | 5 | 0 |
| Slight Browning | 5.1 | 15 | 50 |
| Moderate Browning | 15.1 | 25 | 75 |
| Serious Browning | 25.1 | 100 | 100 |

Defect is calculated based upon L less than 45. Define the min (0) and maximum range (45). Find the L values in the min and max range. Find percentage by dividing by the number of found L values to total L values. Compare data with the defect matrix in Table 4. Match the defect with the ranges of the browning index. If matched then find the shelf life loss from the given percentage loss. Subtract this calculated percentage lost shelf life from the Remaining Shelf Life. In this example, the browning index was less than 2%, hence the Remaining Shelf Life is 12 days.

Based on this analysis, the method predicts the exact maturity stage and remaining shelf life. This information can be used to determine whether the mango is suitable for export or should be distributed locally, reducing losses due to overripe or spoiled fruit.

Example 2. a Banana Photo is Taken as in FIG. 4a on a Tree

The image is resized and cropped. Conduct analysis using Table 6 based upon the following:

a. Based on A max b. Based on A min c. Based on Average Values

Black-White Defect

Maturity stage calculation-if stage is 1 then product ready for harvesting.

TABLE 5

| CIELAB and RGB Parameters for the Banana Photo taken | | | | | | | | | |
|---|---|---|---|---|---|---|---|---|---|
| R | G | B | L | A | B | HUE | HUEMIN | HUEMAX | Defect % |
| 255 | 255 | 255 | 85.2254 | 85.2523 | -27847 | 44.2865 | 117.23 | 117.23 | 0 |
| 254 | 254 | 252 | 68.667 | 68.6567 | -30.075 | 59.1601 | 116.95 | 116.95 | 0 |
| 255 | 255 | 255 | 81.8865 | 81.8865 | -19.315 | 40.0035 | 115.773 | 115.773 | 0 |
| 255 | 255 | 255 | 77.9736 | 77.9736 | -33.306 | 64.8766 | 117.175 | 117.175 | 0 |
| 255 | 255 | 255 | 74.4756 | 74.4756 | -30.58 | 66.7264 | 114.621 | 114.621 | 0 |
| 255 | 255 | 255 | 82.905 | 82.905 | -21.456 | 38.7684 | 118.962 | 118.962 | 0 |
| 243.815 | 246.609 | 235.376 | 76.8641 | 76.8641 | -27.878 | 56.6651 | 116.196 | 116.196 | 0 |

For finding if there is any disease on the banana read the disease file data, which is shown in Table 6. First the Amax from Table 1 is matched with Amax from Table-. For matching we calculate difference of calculated AMAX with each disease's7 AMAX from Table 6 and then taking the stage with least difference. After that we match AMIN using same above technique. Then we check if day calculated from AMAX and AMIN are same. If same then that's the maturity stage if not same then we will compare HUEAVG and HUEMAX further to decide disease.

Suppose the AMAX and AMIN matched with Stage 3, Stage 4 and to Stage 5 respectively, so now we will match AMIN and AMAX for these stages from stage 3 to stage 5

Match calculated HUEMAX with Table 6-'s HUEMAX for stage 3. Match calculated HUEAVG with Table-'s HUEAVG for stage 3. Find and save value which has least difference from above two values Repeat above three steps for all the stages from stage 3 to stage 5. This gives total 3 least values corresponding to stages 3, 4 and 5.

Find the minimum difference value among all the calculated values among above three values. This is our disease that is closest to our calculated value. We found no disease on the banana.

TABLE 6

| Disease Matrix - for Banana | | | | | |
|---|---|---|---|---|---|
| Disease | AMAX | AMIN | HUEMAX | HUEMIN | HUEAVG |
| Anthracnose, Medium | 29 | −17 | 103 | 68 | 87.7 |
| Anthracnose, Severe | 37 | −18 | 310 | 90 | 59.6 |
| Crown Rotting | 26.9 | −17.4 | 294 | 22.9 | 71.2 |
| Gray Mold | −29 | 12.3 | 298 | 68 | 116.7 |
| Fusarium Roseum | 38.6 | −31 | 353 | 61.5 | 88.8 |
| Healthy | −3.3873 | −34.5897 | 140.27 | 102.2007 | 121.9718 |

TABLE 7

| | | Maturity Matrix - for Banana | | | |
|---|---|---|---|---|---|
| Stage | AMAX | AMIN | HUEMAX | HUEMIN | HUEAVG |
| STAGE 1 | −3.3873 | −34.5897 | 140.27 | 102.2007 | 121.9718 |
| STAGE 2 | −3.2526 | −31.906 | 124.5533 | 96.8086 | 111.9377 |
| STAGE 3 | 22.1084 | −26.7638 | 115.8208 | 21.4318 | 100.6394 |
| STAGE 4 | 9.4485 | −19.3766 | 108.0123 | 76.3147 | 93.3819 |
| STAGE 5 | 17.3249 | −10.0394 | 99.3006 | 66.5324 | 89.186 |
| STAGE 6 | 12.3982 | −4.1874 | 93.5746 | 77.3122 | 88.726 |
| STAGE 7 | 22.2797 | −7.5335 | 108.8402 | 11.2733 | 83.7259 |

What is claimed is:

1. A computer-implemented method for predicting a remaining shelf life of a fruit or vegetable, wherein at least one processor and at least one memory are configured to perform the method comprising:

capturing, using an image capture device, an image of said fruit or vegetable;

cropping and resizing the image to isolate an area of interest;

separating Red, Green, and Blue (RGB) channels of pixel values corresponding to the cropped image, and dissecting the cropped image into a plurality of CIELAB color space values using the separated RGB channels;

comparing the dissected CIELAB color space values with predefined CIELAB color space values corresponding to the type of said fruit or vegetable, the predefined CIELAB color space values being organized into separate predefined shelf-life, defect, and maturity matrices;

wherein comparing the dissected CIELAB color space values comprises:

matching at least a Hue-max pixel value of the dissected CIELAB color space values with a known Hue-max pixel value of the predefined maturity matrix; and matching at least a Hue-avg pixel value of the dissected CIELAB color space values with a known Hue-avg pixel value of the predefined maturity matrix;

wherein the predefined maturity matrix correlates a plurality of maturity stages of the type of said fruit or vegetable with a plurality of ranges of predefined CIELAB color space values;

predicting a remaining shelf life of said fruit or vegetable based on the comparison of the dissected CIELAB color space values with the predefined shelf-life, defect, and maturity matrices;

and transmitting the predicted remaining shelf life to an automated system comprising at least one of a drone-based monitoring system or a robotic arm.

* * * * *